US012685662B2

(12) United States Patent
Traversone

(10) Patent No.: US 12,685,662 B2
(45) Date of Patent: Jul. 21, 2026

(54) ADAPTIVE GARMENT FOR OSTOMATE

(71) Applicant: Mary Jo Ellen Traversone, Lockport, NY (US)

(72) Inventor: Mary Jo Ellen Traversone, Lockport, NY (US)

( * ) Notice: Subject to any disclaimer, the term of this patent is extended or adjusted under 35 U.S.C. 154(b) by 363 days.

(21) Appl. No.: 18/442,806

(22) Filed: Feb. 18, 2024

(65) Prior Publication Data

US 2024/0293252 A1     Sep. 5, 2024

Related U.S. Application Data

(60) Provisional application No. 63/436,496, filed on Mar. 1, 2023.

(51) Int. Cl.
*A61F 5/449* (2006.01)
*A61F 5/44* (2006.01)

(52) U.S. Cl.
CPC ............ *A61F 5/449* (2013.01); *A61F 5/4408* (2013.01)

(58) Field of Classification Search
CPC ............................... A61F 5/449; A61F 5/4408
See application file for complete search history.

(56) References Cited

U.S. PATENT DOCUMENTS

| | | | | |
|---|---|---|---|---|
| 4,495,662 A | * | 1/1985 | Miller | A41D 13/1254 2/919 |
| 4,888,006 A | * | 12/1989 | Beaupied | A61F 5/445 2/406 |
| 5,135,520 A | * | 8/1992 | Beaupied | A61F 5/449 604/345 |
| 6,110,156 A | * | 8/2000 | Mendonca | A61F 5/445 604/345 |
| 6,202,222 B1 | * | 3/2001 | Robbins | A41D 13/1254 2/400 |
| 7,313,832 B2 | * | 1/2008 | Worsoee | A61F 5/449 2/400 |
| 7,421,743 B1 | * | 9/2008 | Wixom | A41D 13/1236 604/179 |
| 11,600,200 B2 | * | 3/2023 | Hare | A41D 13/129 |
| 11,766,081 B2 | * | 9/2023 | Thomas | A41D 13/1254 2/69 |
| 2002/0016578 A1 | * | 2/2002 | Gupton | A61F 5/4408 604/345 |
| 2006/0135919 A1 | * | 6/2006 | Worsoee | A61F 5/449 604/345 |
| 2006/0156450 A1 | * | 7/2006 | McGrath | A41D 13/129 2/114 |
| 2006/0189952 A1 | * | 8/2006 | Worsoee | A61F 5/449 604/345 |
| 2014/0196189 A1 | * | 7/2014 | Lee | A61F 5/449 2/69 |
| 2020/0214371 A1 | * | 7/2020 | Apelt | A61F 5/449 |
| 2022/0331144 A1 | * | 10/2022 | Richards | A61F 5/4408 |

(Continued)

*Primary Examiner* — Guy K Townsend

(57) ABSTRACT

Normal clothing adapted to provide access point(s) for the pass through of an ostomy bag/appliance in which the invention provides a barrier between the ostomy appliance and the skin. Method of determination of garment access point(s). The embodiment of the invention results in the garment positioned between the body and the ostomy appliance, promoting access to the stoma and the stoma appliance. The garment is worn over the shoulders and under the ostomy appliance Configured to attain maximum stretching in the vertical direction.

7 Claims, 3 Drawing Sheets

(56)     References Cited

U.S. PATENT DOCUMENTS

| | | | |
|---|---|---|---|
| 2022/0339022 A1* | 10/2022 | Weche | A61F 5/448 |
| 2023/0240883 A1* | 8/2023 | Apelt | A41D 13/1245 |
| | | | 604/345 |
| 2024/0041637 A1* | 2/2024 | Richards | A41D 13/1254 |
| 2024/0284998 A1* | 8/2024 | Dorrough | A41D 13/1245 |
| 2024/0293252 A1* | 9/2024 | Traversone | A61F 5/4408 |
| 2024/0358553 A1* | 10/2024 | Wijay | A61F 13/148 |
| 2025/0099291 A1* | 3/2025 | Mosey | A61F 5/449 |

* cited by examiner

ADAPTIVE GARMENT FOR OSTOMATE

BACKGROUND/SUMMARY

Field of the Invention

The present invention relates to a garment that is worn by Ostomates when ostomy/colostomy/urostomy bag is in use. The invention relates to an undergarment with an opening allowing access to ostomy appliance through the adaptive garment, passthrough of ostomy appliance outside adaptive garment and removal of ostomy bag while providing additional range of motion and method to determine placement of the access point.

Background of the Invention

Ostomy surgery (Colostomy, Ileostomy and Urostomy) is a procedure which leaves an opening called the stoma in the abdominal wall of the patient. Patients who undergo such procedure need to use an ostomy bag/appliance to collect bodily waste/discharge. The ostomy bag can be permanent or temporary. The procedure greatly changes the lives of patients who undergo this surgery. There is a need for garments to normalize the lives of the ostomy patient. Garments and appliances currently in production do not facilitate range of motion or promote thermoregulation. This invention will promote the Ostomate's ability to perform activities of daily living.

The present invention provides a one-piece undergarment with an opening provides access for pass through of the ostomy appliance.

SUMMARY OF THE INVENTION

This Summary is provided to introduce a selection of concepts in a simplified form that is further described below in the Detailed Description Of The Invention. This Summary is not intended to identify key aspects or essential aspects of the claimed subject matter. This Summary is not intended for use as an aid in determining the scope of the claimed subject matter.

The present application discloses an adaptive undergarment that is worn between the ostomy appliance and the epidermis. The ostomy appliance is attached to a flange that is placed over the stoma area. The adaptive garment provides a barrier between the skin, ostomy bag, ostomy belt and other ostomy appliance parts.

The objective of this invention is to provide the ostomate an adaptive garment that provides comfort, reduces dermal breakdown, acts as a barrier when ostomy belt and or ostomy bag is in use, reduces perspiration and helps to maintain body temperature while increasing range of motion.

Another object of this invention is to provide an undergarment constructed from fabric which may comprise one or more layers, that consists of cotton, polyester, spandex, cotton-poly blend, jersey-knit cotton, micro-merino wool, which helps maintain body temperature. However, it will be understood that any type of fabric, whether man-made or natural, coated, raw fiber, disposable or re-usable, may be used without departing from the spirit of the invention.

It is another object of this invention to provide a protective layer between the skin and the ostomy belt, which is used for abdominal wall support to reduce hernias.

The garment consists of an access point sewn into the garment for pass through of the ostomy bag. The opening eliminates the need for a separate urostomy tube hole. The garment is adapted to allow access to the abdominal area of the user.

Another object of this invention is to provide a level of discreetness for those who have undergone an ostomy procedure.

These together with other objects and advantages will become subsequently apparent, reside in the details of the invention as more fully described and claimed, reference being had to the accompanying drawings forming a part thereof, wherein line numerals refer to parts throughout.

DESCRIPTION

Brief Description of the Drawings

The novel feature of the invention, as well as the invention itself, both as to its structure and its operation/location will best be understood from the accompanying drawings, taken in conjunction with the accompanying description.

DETAILED DESCRIPTION OF THE INVENTION

Figure 1:
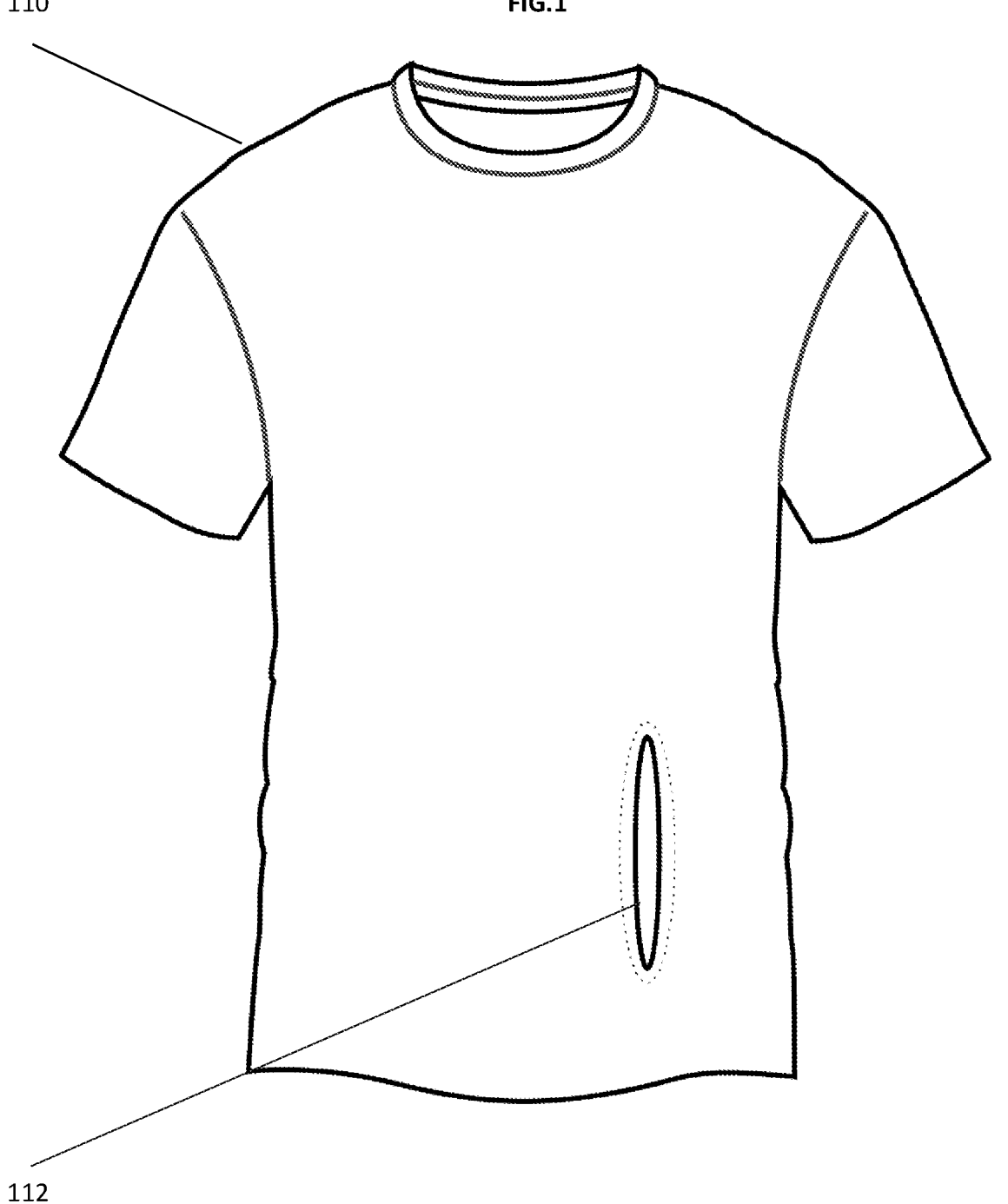
FIG. 1 is a front view of the ostomy garment reflecting the preferred embodiment of the invention as worn by the user of the ostomy appliance.

What follows is a description of various aspect, embodiment and/or examples in which the invention may be practiced. Reference will be made to the attached drawing and the information included in the drawing is a part of this detailed description. The aspects, embodiments and/or examples described herein are presented for exemplification purposes, and not for limitation purposes. Structural and/or logical modifications could be made by someone of ordinary skill in the art without departing from the scope of the invention.

FIG. 1 shows a full-frontal view of the undergarment (110) according to the present invention. As shown in FIG. 1 the present invention is comprised of an opening (112) on a garment (110) that is positioned vertically and for wearer needs could be positioned horizontally or any direction thereof.

Figure 2:
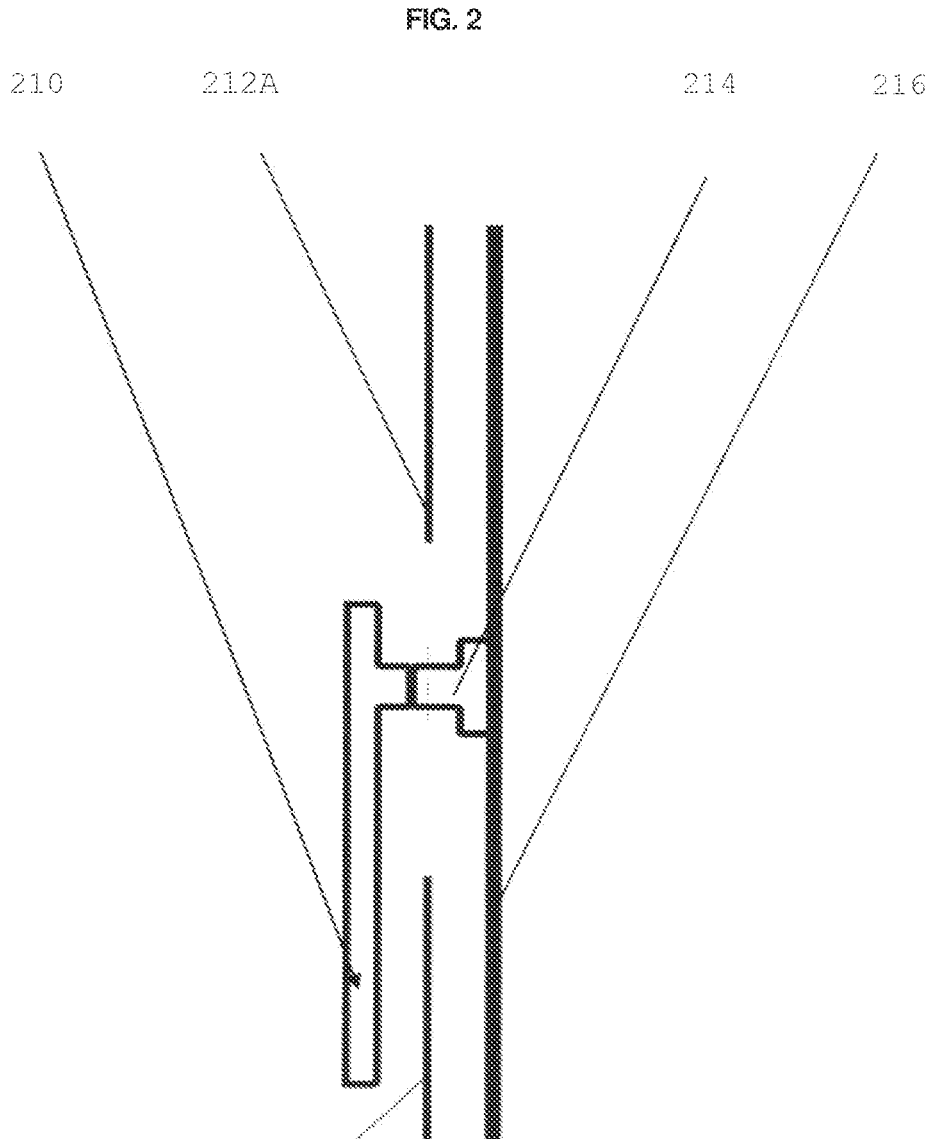
FIG. 2 is a side view of one type of ostomy appliance suitable for use with the present invention.

As Shown in FIG. 2 Reflects a side view of the invention providing a layer of fabric between the wearer's skin and ostomy appliance. The body of the wearer (216) is protected by the present invention (212A/212B) with the ostomate's flange (214) and ostomy bag/appliance (210) inserted through the access point.

Figure 3:
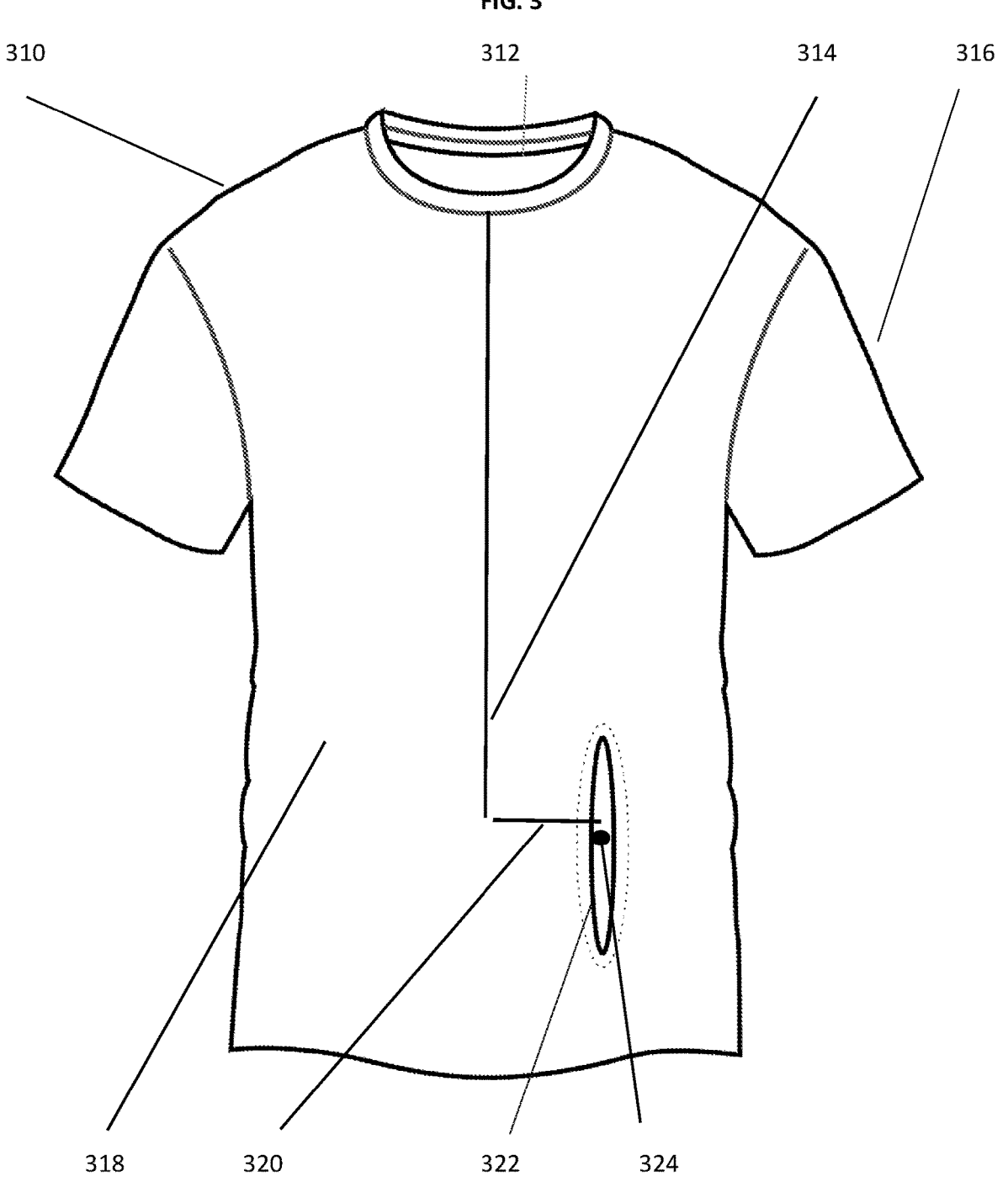
FIG. 3 is a front view of a second representation of the invention. To accommodate appliance in various positions relative to the wearer's body, location of access point can be adapted to accommodate both left and right stoma placement.

As shown in FIG. 3 For ease of construction, the garment (310) is symmetrical about the longitudinal midlines, although this is not intended to present a constraint on the design. The garment has the appearance of an everyday undergarment, complete with sleeves (316), neck hole (312) and garment body (318). The garment may also be sleeveless without departing from the spirit of the invention, but preference is given to the incorporation of the sleeves (316) for purposes of retaining the patient's body heat. The undergarment can be short or long sleeved or of body suit style. Furthermore, the semi-fitted nature of the garment (310) does not allow for significant volume of air-flow between the patient's body, garment body (318) and the ambient environment. FIG. 3 also reflects method to determine placement of access point (322) which is calculated by measurement of distance from the suprasternal notch and pelvic area (314), in relation to the stoma (324). The distance from midline intersection to the stoma (324) (left or right side) to be identified. (3) This sizing method can be used for all sizes/ages from infant to adult.

The present invention seeks to remedy the problems created by existing garments by amending the garment and creating improved garment functionality through use of materials which have the requisite insulative and heat-retentive characteristics. The invention provides the ostomy patient use of normal clothing for personal comfort, to promote psychological and physiological wellbeing and provide a greater range of motion by use of access point in the undergarment.

Adaptive access point to be surged/sewn to allow for long term use of undergarment. Size of adaptive access point(s) will vary based on age/size of the user. The access point can be circular, oval, oblong, rectangular, triangular, diamond, oval shaped or of variation.

Adaptive access point to allow range of motion/greater flexibility. Adaptive opening will vary based on size of ostomate (generally 3"-12").

The Adaptive Undergarment for Ostomate is to be worn under ostomy bag to reduce irritation, skin breakdown, reduce perspiration, maintain body temperature, and provide comfort to the wearer.

For those patients that struggle with maintaining body temperature, the Adaptive Undergarment For Ostomate can be tucked into pants, skirts, etc. then layered with an outer shirt for fashion purposes. Undergarment can be of tank top or T-Shirt style (racer back, long sleeve, short sleeve, tank bra, etc).

The undergarment of the present invention is designed for both male and female users and the invention works for multiple types of drainable and closed ostomy bags. Furthermore, the access point can fit bags with variable lengths, shapes, and sizes.

While many of the fundamental characteristics and features of the undergarment have been described herein, with reference to embodiment thereof, a latitude of modification, various changes and substitutions are intended in the foregoing disclosures, and it should be apparent that in some instances some features of the invention will be employed without a corresponding use of other features without departing from the scope of the invention. Consequently, all such modifications and variations are included within the scope of the invention as defined herein.

The invention claimed is:

1. A method for providing a custom fit one-piece undergarment comprising at least one ostomy bag opening to at least one stoma of an ostomy patient; the method comprising:

providing a one piece undergarment;

measuring a first line starting from the suprasternal notch of the patient toward an inferior edge of the one-piece undergarment;

measuring a second line perpendicular to the first line, where the second line bisects the corresponding stoma providing the ostomy bag opening in the one-piece undergarment located at an intersection of the first line and the second line, the ostomy bag opening providing an access point for pass through for attaching or removing the ostomy bag to or from the at least one stoma, the resulting custom fit one-piece undergarment configured for acting as a barrier between skin of the wearer and the ostomy bag;

providing the resulting custom fit one-piece undergarment comprising the ostomy bag opening that is custom fit to provide the ostomy bag opening for the access point for the pass through of the ostomy bag to attach or detach from the at least one stoma and to provide a barrier between the skin of the wearer and the ostomy bag.

2. The method of claim 1, wherein said custom fit one-piece undergarment comprises two or more ostomy bag openings.

3. The method of claim 2, wherein one or more locations and sizes of said at least one ostomy bag opening in said custom fit one-piece undergarment is sized and located on said custom fit one-piece undergarment is based on the wearer's size, age, and location of the at least one stoma.

4. The method of claim 3, wherein edges of the custom fit one-piece undergarment forming the ostomy bag opening comprise sewing or surging configured to stabilize a fabric of said custom fit one-piece undergarment around said bag opening.

5. The method of claim 4, wherein the at least one ostomy bag opening is configured to provide additional range of motion of the custom fit one-piece undergarment for the wearer wherein the combination of the one-piece undergarment and the at least one ostomy bag opening is configured to provide a more stable body temperature and reduced dermal irritation of the resulting custom fit one-piece undergarment.

6. The method of claim 3, wherein the one or more locations of said at least one ostomy bag opening comprise the intersection of (a) the first line starting from the suprasternal notch and ending at the inferior edge of the shirt; and (b) the second line substantially perpendicular to the first line, wherein the second line bisects the corresponding stoma.

7. At least one custom fit one-piece undergarment provided according to the method of claim 1.

\* \* \* \* \*